United States Patent [19]

Häring

[11] Patent Number: 4,990,642
[45] Date of Patent: Feb. 5, 1991

[54] PROCESS FOR PREPARING OXIMOSILANES

[75] Inventor: Horst Häring, Martinistrasse 82, D-8900 Augsburg 21, Fed. Rep. of Germany

[73] Assignee: Horst Haring, Ausberg, Fed. Rep. of Germany

[21] Appl. No.: 273,859
[22] PCT Filed: Feb. 2, 1988
[86] PCT No.: PCT/DE88/00049
 § 371 Date: Mar. 31, 1989
 § 102(e) Date: Mar. 31, 1989
[87] PCT Pub. No.: WO88/05778
 PCT Pub. Date: Aug. 11, 1988

[30] Foreign Application Priority Data

Feb. 5, 1987 [DE] Fed. Rep. of Germany ....... 3703484

[51] Int. Cl.$^5$ ............................. C07F 7/10; C07F 7/18
[52] U.S. Cl. ................................................ 556/422
[58] Field of Search ..................................... 556/422

[56] References Cited

U.S. PATENT DOCUMENTS

| | | | |
|---|---|---|---|
| 3,189,576 | 6/1965 | Sweet | 556/422 X |
| 3,448,136 | 6/1969 | Paude et al. | 556/422 X |
| 3,697,568 | 10/1972 | Boissieras et al. | 556/422 |
| 4,033,991 | 7/1977 | Shinohara et al. | 556/422 X |

Primary Examiner—Paul F. Shaver
Attorney, Agent, or Firm—Wegner, Cantor, Mueller & Player

[57] ABSTRACT

Described is a process for producing oximosilanes having the general formula (I)

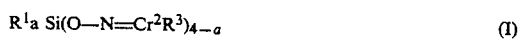

wherein $R_1$ represents a straight-chain or branched alkyl residue having between 1 and 18 carbon atomns, a straight-chain or branched alkenyl residue having between 2 and 18 carbon atoms, an aryl or aralkyl residue optionally substituted by halogens, nitro groups, amino groups and/or alkyl residues having between 1 and 4 carbon atoms, or a straight-chain or branched alkoxy-residue having between 1 and 8 carbon atoms, a is an integer of 0 to 3, and $R^2$ and $R^3$, independently of each other, represent straight-chain or branched alkyl residues having between 1 and 18 atoms, optionally substituted by halogens, nitro groups, amino groups and/or alkyl residues having between 1 and 4 carbon atoms, by reacting an acyloxisilane with an oxime in molar excess, characterized in that an acyloxy-silane of general formula (II)

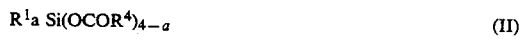

wherein $R^1$ and a have the above mentioined significations and $R^4$ represents straight-chain or branched alkyl residues having between 1 and 18 carbon atoms, preferably between 2 and 8 and more preferably between 2 and 4 carbon atoms, straight-chain or branched alkenyl residues having between 2 and 18 carbon atoms or aryl or aralkyl residues optionally substituted with halogens, nitro groups, amino groups and/or alkyl residues having between 1 and 4 carbon atoms, with a ketoxime having the general formula (III)

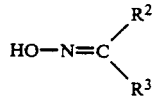

wherein $R^2$ and $R^3$ possess the above significations, in the absence of an acid acceptor, while distilling off the carboxylic acid, which is released from the acyloxisilane of the general formula (III).

4 Claims, No Drawings

PROCESS FOR PREPARING OXIMOSILANES

The subject of the present invention relates to the production of oximosilanes by a rapid, economical and safe method that obviates the use of solvents.

It is known that oximosilanes can be produced by inducing a reaction of organochlorosilanes with oximes in the presence of suitable acid acceptors and solvents (U.S. Pat. Nos. 3,962,160, 3,441,583, 3,341,486, 3,817,909, DE-AS 13 01 140, DE-AS 11 20 690, DE-AS 12 55 924, FR-PS 11 18 495, EP-PS 0 036 262, W. Noll, Chemie und Technologie der Silikone, Seite 342, Verlag Chemie, Weilheim 1968).

The byproducts resulting from the use of this known method will be, depending upon the acid acceptor employed, quaternary ammonium salts such as ammonium chloride or amine hydrochloride. Due to the inevitable formation of such salts during the reaction, it is necessary, in order to be able to produce an acceptable crystal paste, that a large quantity of solvent be added to act as a surfactant. After the reaction has ended, the resulting oximosilane is separated from the salt formed during the reaction, and the salt then washed with large quantities of solvent. The fact that these salts cannot be economically washed away gives rise to the great dsadvantage that a considerable quantity of the desired end product, i.e. oximosilane, is absorbed onto their surface.

The desired oximosilane, which is contained in the filtrate, remains in the bottoms after the solvent is driven off. Subsequent distillation of the oximosilane yields the pure end product.

It has been shown, in practice, that residues containing such salts and present in the oximosilane bottoms can, during the subsequent distillation procedure, cause the explosive disintegration of the oximosilane through a Beckmann rearrangement. This phenomenon has been treated in the report of Leslie J. Tyler, Vice President and Research Director of Dow Corning Company, (published in C+E News, issue of 2/9/1974).

The literature describes a number of processes that avoid the formation of such salts. In this vein, DE-OS 27 19 008 sheds light on the reaction of a substituted aminosilane, e.g. ethyl tri(cyclohexylamino) silane or methyl-tri (secondary butyl-amino) silane with methyl ethylketoxime, whereafter the thus formed cyclohexylamine or secondary butylamine is distilled off so as to produce a ketoximsilane, whereby the residual distillate, the oximosilane, can be used without further treatment to produce coloured or transparent silicon sealants. Such a process does not, however, solve the present problem, because the offending salts, already issuing from the production of the aminosilanes, renders this method, too, uneconomical.

Described in JP-PS 80-016008 (C.A. (1980), 92-199928) is the reaction of alkoxisilanes, preferably silicontetraalkoxisilanes aided by a transesterification catalyst from the cyclo-diaza undazene series, with ketoximes. It has been shown, however, that the rather sluggish advance of such reactions coupled with the formation of a plurality of different substitute products causes such reactions to be extremely slow. Such reactions, moreover, being ineffective facilitators of alkoxi group replacement, render the corresponding process incapable of providing an economical solution to the difficulties related to the production of tetra and trifunctional oximosilanes.

U.S. Pat. Nos. 3,697,568 describes iminoxiorganosilanes and a process for their production. Such iminoxisilanes distinguish themselves from the substance produced according to the invention in that they feature not only the oxime residue but also an additional glycolether residue. In order to produce such compounds, either a halogen silane or an acyloxisilane is converted with an oxime in the presence of ammonia or a primary alkylamine or arylamine in an inert diluent (claims 12 and 13). As illustrated by the examples given, the use of a nitrogen-containing base in an inert diluent for the purpose of enabling the reaction to completely run its course, is an unavoidable necessity. Example 6 of this publication describes the reaction of methyltriacetooxisilane with an acetaldehydeoxime, in which acetic acid and volatile products are first distilled off, and then to facilitate the reaction with the monomethylether of ethylene glycol in the presence of ammonia, is brought to completion.

After this reaction has run its course, the ammonium salt-containing bottom is, as in other similar processes, filtered out and washed with an organic solvent. This known process also produces large quantities of quaternary ammonium salts that, as has been demonstrated above, are able to cause, during the subsequent distillation of the solvent or the end product, an explosive disintegration of the oximosilane due to Beckmann rearrangement.

The objective of the present invention is thus the identification of a process which, while it does not involve the use of solvents, is capable of producing the required oximosilanes without engendering harmful solids, i.e. quaternary ammonium salts, such a process being assisted by a relatively rapid and economical method and thereby being capable of avoiding the explosive disintegration of the oximosilane through Beckmann rearrangement.

This objective has been shown to be attainable if an acyloxisilane is caused to react with a ketoxime without the use of an acid acceptor and if the carboxylic acid released from the acyloxisilane is removed by distillation.

The objective of the invention is thus the creation of a process suitable for producing oximosilanes of the general formula (I)

$$R^1{}_a Si(O-N=CR^2R^3)_{4-a} \qquad (I)$$

wherein $R^1$ represents a straight-chain or branched alkyl residue having between 1 and 18 carbon atoms, a straight-chain or branched alkenyl residue hving between 2 and 18 carbon atoms, an aryl or aralkyl residue substituted with halogens, nitro groups, amino groups and/or alkyl residues having between 1 and 4 carbon atoms, or a straight-chain or branched alkoxy residue having between 1 and 8 carbon atoms, a is an integer of 0 to 3 and $R^2$ and $R^3$ represent, independently of each other, straight-chain or branched alkyl residues having between 1 and 18 carbon atoms, optionally substituted with halogens, nitro groups, amino groups and/or alkyl residues having between 1 and 4 carbon atoms by reaction of an acyloxysilane with an oxime in molar excess, characterized in that an acyloxisilane of the general formula (II)

$$R^1{}_a Si(OCOR^4)_{4-a} \qquad (II)$$

in which $R^1$ and a have the above significations and $R^4$ represents straight-chained or branched alkyl residues having between 1 and 18 carbon atoms, straight-chain or branched alkyl residues having between 2 and 18 carbon atoms or aryl or aralkyl residues optionally substituted with halogens, nitro groups, amino groups and/or alkyl residues having between 1 and 4 carbon atoms, is reacted with a ketoxime having the general formula (III)

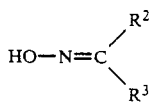

wherein $R^2$ and $R^3$ have the above significations, without the use of an acid acceptor, and wherein carboxylic acid(s) released from the acyloxisilane having the general formula (III) is removed by distillation.

Such a process, which does not require the use of solvents, allows a high rate of recovery of a desired oximosilane of greater purity. The continuous distilling-off of the carboxylic acid released during the reaction permits the reaction to continue to equilibrium. Thus, the Beckmann rearrangement is precluded, since during the process according to the invention, neither acids are used nor quaternary ammonium salts formed. Thus, the proposed procedure offers a safe and economically attractive means of producing oximosilanes.

In the process according to the invention it is preferable to use acyloxisilanes of the above-mentioned general formula (II) in which the $R^1$ groups represent alkyl residues having between 1 and 8, more preferably between 1 and 4 carbon atoms, in particular methyl or ethyl residues, alkene residues having between 2 and 8 carbon atoms, in particular vinyl residues, if necessary phenyl-naphthyl or benzyl residues substituted singly or in multiple fashion by halogens, such as in particular chlorides or bromides, nitro groups, amino groups and-/or alkyl residues having between 1 and 4 atoms, and the $R^4$ groups represent alkyl residues having between 2 and 8, more preferably between 2 and 4 carbon atoms, in particular ethyl residues, while in the oximes having the general formula (III) the groups $R^2$ and $R^3$ preferably represent hydrogen atoms or alkyl residues having between 1 and 8 carbon atoms, more preferably between 1 and 4 carbon atoms, in particular methyl residues or ethyl residues.

It is especially preferable to employ in the role of acyloxisilane having the general formula (II), vinyl, methyl or ethyltriaceto-oxisilanes that result in conjunction with usable process byproducts. Oximes having the general formula (II) are preferably methyl-ethyl ketoximes or dimethyl ketoximes that are also commercially available and especially well-suited for the process according to the invention.

In the process according to the invention, the reaction should take place at a temperature situated preferably between 20° and 60° C., at which temperature the reaction runs spontaneously until chemical equilibrium is reached. If, during the reaction, carboxylic acid released from the acyloxisilane of the general formula (II) is distilled off, the reaction, as already mentioned, will proceed to 100% completion.

It is particularly advantageous for the reaction and the distillation of the carboxylic acid to take place under reduced pressure. It is especially desirable if the reaction is carried out at a temperature situated between 30° and 120° C. and the container evacuated to a pressure situated between 0.1 and 100 millibars, whereby a mixture of oxime and released acid, preferably acetic acid, is distilled off.

In order to facilitate the reaction, the oxime having the general formula (III) can be used in a 1 to 4M concentration.

The carboxylic acid which is distilled off during the process according to the invention and contains more or less large portions of the oxime used as the feedstock, can be purified in a subsequent recovery process. The resulting pure carboxylic acid and the unconverted oxime can be used again as feedstocks in the process according to the invention.

After the acetic acid has been distilled off in a vacuum of between 0.1 and 100 millibars and at a temperature of between 50° and 80° C., an oximosilane is obtained, whose purity permits the material to be used in coloured or transparent silicon sealants. It is, however, possible to purify the oximosilane bottom through subsequent distillation at low pressure. It is thus possible to obtain a colourless, very pure oximosilane that can be employed in all known applications.

The process according to the invention can be carried out in a continuous, semi-continuous, or intermittent manner. Although the process according to the invention does not require the use of solvents, the employment of the latter, especially in the role of carrier for the carbonic acid formed during the reaction, need not be excluded. Preferred solvents for this purpose are chlorinated aliphatic compounds such as perchloroethylene or trichloroethylene.

EXAMPLE

1 Mol methyl-tris(acetoxil)-silane is weighed in a 1 liter three-necked flask equipped with a stirring device, a dripping funnel and a distilling tube with a vacuum lock. In order to ensure the complete removal of air, the container is washed with nitrogen. The solid methyl-tri(acetoxi)-silane is then heated to a temperature situated between 40° to 60° C. and the flask is evacuated until a pressure of 1 millibar is reached, whereafter for approximately 1 hour 8 mols of methyl-ethyl-ketoxime are added through the dripping funnel fitted with a vacuum compensator. As soon as the methyl-ethyl-ketoxime is added, the distillation of a mixture of ketoxime and acetic acid begins.

The substitution of the acetate groups by ketoxime groups can be monitored with the help of a gas chromatograph, whereby after the completion of the reaction, the excess ketoxime is removed by distillation under vacuum at a temperature situated between 60° and 90° C. Obtained through a practically quantitative reaction relative to the methyl-tri(acetoxi)-silane employed, the end product, i.e. the methyl-tri(methyl-ethyl-ketoximo)-silane, has the form of a weak yellowy to browny coloured liquid which, during the subsequent distillation procedure at temperatures situated between 120° and 130° C. and 1 millibar, appears as a colourless liquid that still features between 6 and 10% dimer or trimer components.

I claim:

1. Process for the formation of oximosilanes of the general formula (I)

wherein $R^1$ represents a straight-chain or branched alkyl residue having between 1 and 18 carbon atoms, a straight-chain or branched alkenyl residue having between 2 and 18 carbon atoms, an aryl or aralkyl residue optionally substituted with one or more members of the group consisting of halogens, nitro groups, amino groups and alkyl residues having between 1 and 4 carbon atoms, or a straight-chain or branched alkoxy-residue having between 1 8 carbon atoms, a is an integer of 0 to 3 , and $R^2$ and $R^3$, independently of each other, represent straight-chain or branched alkyl residues having between 1 and 18 carbon atoms, optionally substituted with halogens, nitro groups, amino groups and alkyl residues having between 1 and 4 carbon atoms by a reaction of an acyloxysilane with an oxime in molar excess, comprising reacting an acyloxysilane of the general formula (II)

$$R^1{}_a\,Si(OCOR^4)_{4-a} \qquad (II)$$

wherein $R^1$ and a have the above-indicated significations and $R^4$ represents straight-chain or branched alkyl residues having between 1 and 18 carbon atoms, straight-chain or branched alkenyl residues having between 2 and 18 carbon atoms or aryl or aralkyl residues which may be substituted with halogens, nitro groups, amino groups and alkyl residues having between 1 and 4 carbon atoms, with a ketoxime of general formula (III)

wherein $R^2$ and $R^3$ have the above significations, in the absence of an acid acceptor, while distilling off carboxylic acid, released from the acyloxysilane of the general formula (II).

2. A process according to claim 1, characterized wherein the reaction is carried out at a temperature in the region between 20° and 60° C.

3. A process according to claim 1, wherein the reaction and the distilling-off of the released carboxylic acid are carried out at a temperature between 30° and 120° C. and at a pressure between 0.1 and 100 millibars.

4. A process according to claim 1, wherein the oxime having the general formula (III) is present in a 1 to 4 molar excess.

* * * * *